(12) United States Patent
Blazewicz et al.

(10) Patent No.: US 11,001,751 B2
(45) Date of Patent: May 11, 2021

(54) CROSSLINKED POLYMERS DERIVED FROM MONOMERS HAVING ACRYLOYL AND LACTAM MOIETIES AND SULFONIC ACID/SULFONATE COMONOMERS, COMPOSITIONS THEREOF, AND APPLICATIONS THEREOF

(71) Applicant: HERCULES LLC, Wilmington, DE (US)

(72) Inventors: Ryan Vincent Blazewicz, Lake Hiawatha, NJ (US); Janice Jianzhao Wang, Hockessin, DE (US); Brent R. Gonska, Wilmington, DE (US)

(73) Assignee: HERCULES LLC, Wilmington, DE (US)

( * ) Notice: Subject to any disclaimer, the term of this patent is extended or adjusted under 35 U.S.C. 154(b) by 106 days.

(21) Appl. No.: 15/776,301

(22) PCT Filed: Nov. 18, 2016

(86) PCT No.: PCT/US2016/062673
§ 371 (c)(1),
(2) Date: May 15, 2018

(87) PCT Pub. No.: WO2017/087748
PCT Pub. Date: May 26, 2017

(65) Prior Publication Data
US 2018/0346804 A1 Dec. 6, 2018

Related U.S. Application Data

(60) Provisional application No. 62/258,186, filed on Nov. 20, 2015.

(51) Int. Cl.
| | | |
|---|---|---|
| C09K 8/88 | (2006.01) |
| A23L 29/00 | (2016.01) |
| A61K 8/81 | (2006.01) |
| A61K 31/79 | (2006.01) |
| A61Q 19/00 | (2006.01) |
| C04B 28/02 | (2006.01) |
| C08F 220/58 | (2006.01) |
| E21B 33/14 | (2006.01) |
| A61K 31/787 | (2006.01) |
| C09K 8/035 | (2006.01) |
| C09K 8/467 | (2006.01) |
| A61K 31/795 | (2006.01) |
| C09K 8/68 | (2006.01) |
| C09K 8/512 | (2006.01) |
| C09K 8/24 | (2006.01) |
| C09K 8/487 | (2006.01) |
| C09K 8/575 | (2006.01) |
| E21B 43/12 | (2006.01) |
| C08L 33/26 | (2006.01) |
| C08L 33/14 | (2006.01) |
| C04B 103/00 | (2006.01) |

(52) U.S. Cl.
CPC .............. *C09K 8/887* (2013.01); *A23L 29/00* (2016.08); *A61K 8/8158* (2013.01); *A61K 31/787* (2013.01); *A61K 31/79* (2013.01); *A61K 31/795* (2013.01); *A61Q 19/00* (2013.01); *C04B 28/02* (2013.01); *C08F 220/58* (2013.01); *C09K 8/035* (2013.01); *C09K 8/24* (2013.01); *C09K 8/467* (2013.01); *C09K 8/487* (2013.01); *C09K 8/512* (2013.01); *C09K 8/5756* (2013.01); *C09K 8/685* (2013.01); *E21B 33/14* (2013.01); *E21B 43/12* (2013.01); *A61K 2800/10* (2013.01); *C04B 2103/0036* (2013.01); *C04B 2103/0082* (2013.01); *C08L 33/14* (2013.01); *C08L 33/26* (2013.01); *C08L 2201/54* (2013.01); *C09K 2208/22* (2013.01); *C09K 2208/32* (2013.01)

(58) Field of Classification Search
None
See application file for complete search history.

(56) References Cited

U.S. PATENT DOCUMENTS

| | | | |
|---|---|---|---|
| 3,423,381 A | 1/1969 | Merijan et al. | |
| 6,232,273 B1 | 5/2001 | Namba et al. | |
| 2005/0287191 A1* | 12/2005 | Munro | C08F 2/44 424/443 |
| 2015/0000985 A1 | 1/2015 | Zhou et al. | |
| 2018/0344615 A1* | 12/2018 | Gamez-Garcia | A61Q 5/12 |

OTHER PUBLICATIONS

International Search Report, PCT/US2016/062673 published on May 26, 2017.

* cited by examiner

Primary Examiner — Jeffrey D Washville
(74) Attorney, Agent, or Firm — William J. Davis; Nathalie Tietcheu

(57) ABSTRACT

The invention provides polymers comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker. The invention further provides various compositions comprising the polymers. The invention furthermore provides applications of these compositions in various industrial arts, particularly in oilfield operations such as drilling and cementing.

1 Claim, No Drawings

CROSSLINKED POLYMERS DERIVED FROM MONOMERS HAVING ACRYLOYL AND LACTAM MOIETIES AND SULFONIC ACID/SULFONATE COMONOMERS, COMPOSITIONS THEREOF, AND APPLICATIONS THEREOF

BACKGROUND

Field of the Invention

The invention provides polymers comprising repeating units derived from monomers having at least one functionalized or unfunctionalized acryloyl moiety and at least one lactam moiety, monomers having sulfonic acid and/or sulfonate moiety, and one or more crosslinkers. The invention further provides compositions comprising the polymers and applications thereof in various industrial arts, particularly in oilfield operations.

Description of Related Art

A natural resource such as oil or gas residing in a subterranean formation can be recovered by drilling a well into the formation. To do so, a wellbore is typically drilled down to the subterranean formation while circulating a drilling fluid through the wellbore.

Rotary drilling methods employing a drill bit and drill stems have long been used to drill well bores in subterranean formations. Drilling fluids or muds are commonly circulated in the well during such drilling to cool and lubricate the drilling apparatus, lift drilling cuttings out of the wellbore, and counterbalance the subterranean formation pressure encountered. When penetrating a porous formation, such as an unconsolidated sand, it is well known that large amounts of fluid may be pushed by pressure into the formation. This reduction in the amount of circulating fluid is commonly known as a fluid loss.

The simplest drilling fluid comprises a mixture of drilled solids and water, sometimes referred to as "native" drilling mud. In some instances, the solids obtained consists of clays, which when finally ground, function as the solid component of the drilling fluid or drilling mud. These drilling fluids tend to function reasonably well for controlling normal pressures at shallow depths in many oil and gas wells.

The drilling fluid, cementing fluid or stimulation fluid generally includes a fluid loss control additive to reduce the loss of fluid, e.g., water, from the fluid when in contact with permeable subterranean formations and zones. Fluid loss control plays an important role in those oilfield treatment fluids (fracturing, cementing, gravel/frac packing etc). Most of the treatments use a polymer based fluid (guar, guar derivative or hydroxy ethyl cellulose, etc.) to control leak off. These fluids build a low permeability filter cake that reduces the leak-off rate by reducing the diffusion rate of the solvent across the boundary between the bulk of the fluid and the formation (filter cake). For further decrease in leak-off rate macroscopic solids such as fine silica, calcium carbonate, mica, or clays are added to the fluid. Also, the addition of a second soluble polymer such as polyacrylamide, starch, xanthan, etc to the polymer based fluid is not uncommon to control fluid leak-off.

The addition of various art known compounds to the drilling fluid can minimize fluid loss into the formation. Additionally, the compounds added to the wells to prevent fluid loss must withstand the temperatures in the wells, generally from about 100 to about 500° F. The art refers to materials that function in this way as HPHT fluid loss control aids. Many, however, cannot function adequately at these extreme conditions of temperature and pressure.

Bore hole temperatures can vary from ambient up to about 500° F. and pressures from atmospheric up to about 20,000 psi. Temperature and pressure conditions such as these can have an adverse effect on bore hole fluids causing them to destabilize if they contain additives and furthermore, these pressures and temperatures have a very strong effect in forcing the drilling fluid not only to the surface, but also against the side of the bore hole causing either filtrate loss or a break through of the drilling fluid, as well as the oil or gas under pressure into the permeable strata considerably below the opening of the well at the surface. Accordingly, the industry has sought ways to prevent not only the adverse effect on drilling fluid additives encountered under these conditions, but also blowouts of the well and the subsequent loss of oil, gas or other materials produced in the well, by the use of HPHT additives to the drilling mud.

Accordingly, it would be an advantage to provide a composition as well as a process that minimized or eliminated the foregoing difficulties encountered in additives to drilling fluids, especially HPHT fluid loss control aids.

After the drilling is terminated, a string of pipe, e.g., casing, is run in the wellbore. Primary cementing is then usually performed whereby a cementing fluid, usually including water, cement, and particulate additives, is pumped down through the string of pipe and into the annulus between the string of pipe and the walls of the wellbore to allow the cementing fluid to set into an impermeable cement column and thereby seal the annulus. Subsequent secondary cementing operations, i.e., any cementing operation after the primary cementing operation, may also be performed. One example of a secondary cementing operation is squeeze cementing whereby a cementing fluid is forced under pressure to areas of lost integrity in the annulus to seal off those areas.

As the bottom hole circulating temperature of well increases, the viscosity of a cementing fluid decreases. This decrease in viscosity, which is known as thermal thinning, can result in settling of the solids in the slurry. Undesirable consequences of the solids settling include free water and a density gradient in the set cement. To inhibit settling, cement anti-settling agents, e.g., polymers can be added to the cementing fluid. As the cementing fluid temperature increases, the cement anti-settling agent is thought to increase the viscosity of the cementing fluid. One important feature of an anti-settling agent is that it does not adversely affect low-temperature rheology.

Existing anti-settling agents, e.g., guar or guar derivatives treated with borate, delay crosslink breakage sufficiently to allow mixing and pumping of a cement fluid without imparting an excessively-high viscosity. However for wells that are at depth more than 5000 ft, the temperature of the well increases and could reach 375° F. or higher. Most of additives that work well at lower temperature would lose the viscosity at this temperature range due to chemical instability or other molecular interactions. Sometimes one could compensate for this activity loss by using higher amount of the additive. The technical limit of this approach is, however, that higher additive dosages will cause high viscosity of the mix at the surface condition. Pumping of the cement is difficult when consistency of a mix is higher than 40 BC.

The additive also should not cause free water on top of the slurry of cement when it is sitting before cure. Excessive free water on top of the cement column will result in an incompetent zone close to the top of the liner which will have to be remedied with an expensive squeeze job. The viscosity of the slurry describes the rheological behavior of the slurry, which is determined by measuring the plastic viscosity (pv) and the yield point (yp) of the slurry. The cement slurry should be fluid and pumpable until it is in place, then it should start to set as soon as possible after placement. Any delay in the development of compressive strength will increase the "waiting on cement" time (WOC) necessary before proceeding with the next operation. The thickening time (TT) is used to describe the point at which the gelation of the cement has proceeded to such an extent so as to affect the pumping rates.

U.S. Pat. No. 2,882,262 discloses N-(acryloxyalkyl)- and N-(methacryloxyalkyl)-2-pyrrolidones, polymers thereof, and a process for their preparation. The polymers are particularly useful in the photographic art.

U.S. published patent application 2010/0166985 discloses aqueous dispersions of (meth)acrylic esters of polymers comprising N-hydroxyalkylated lactam units, processes for preparing them, and use of (meth)acrylic esters of polymers comprising N-hydroxyalkylated lactam units for treating paper.

U.S. Pat. No. 5,712,356 discloses a cross-linkable copolymer comprising a copolymerization product of a monomer mixture consisting substantially of a vinyl lactam (a) and at least one further vinyl monomer (b) of a different type. The disclosed polymers are water-soluble and used in the preparation of hydrogel contact lenses. The disclosed more strongly preferred water soluble copolymers comprise a copolymerisation product of a monomer mixture consisting of 60-80 mole % of a vinyl lactam (a) and 20-40 mole % of at least one vinyl monomer (b) and, where appropriate, a reactive vinyl monomer (c).

U.S. Pat. No. 6,683,144 relates to water-soluble or water-swellable crosslinkable copolymers based on ammonium salts of acrylamidoalkylsulfonic acids and cyclic N-vinylcarboxamides or cyclic and linear N-vinylcarboxamides, to the preparation thereof and to the use thereof as thickeners, stabilizers of emulsions and dispersions and as glidants in cosmetic and pharmaceutical compositions.

Published PCT application WO2014071354 discloses a personal care conditioning and/or styling composition for a keratin substrate comprising: (A) at least one conditioning and/or styling polymer obtained by polymerizing (i) about 50 wt. % to 95 wt. % of at least one cationic or pseudo-cationic monomer selected from the group consisting of acrylamidopropyl trimethylammonium chloride (APTAC) and/or Vinylpyrrolidone (VP); (ii) about 1 wt. % to 30 wt. % of at least one anionic monomer selected from the group consisting of (a) acrylic acid (AA), (b) acrylamido methyl-propyl sulfonate (AMPS), and/or (c) sodium methyl allyl sulfonate (SMAS); and (iii) about 0.1 wt. % to 20 wt. % of at least one hydrophobic monomer selected from the group consisting of (a) polyoxyethylene (PEG)-18-behenylether-methacrylate (BEM) (b) Lauryl-ethoxylated-methacrylate (LEM), (c) stearyl acrylate (SA), (d) Stream-10-allyl-ether (BRIJ), (e) vinylcaprolactam (V-Cap), and/or (f) Hydroxy-ethyl-pyrrolidone-methacrylate; (B) at least one cosmetically acceptable excipient; and (C) optionally, at least one effective amount of personal care active ingredient.

U.S. published patent application 2008/0138300 discloses a cosmetic composition comprising, in a cosmetically acceptable medium: at least one acrylic polymer resulting from the copolymerization of: a) at least one monomer A chosen from esters derived from the reaction of (meth) acrylic acid with at least one monoalcohol comprising from 2 to 20 carbon atoms, b) at least one monomer B chosen from esters derived from the reaction of methacrylic acid with at least one monoalcohol comprising from 1 to 10 carbon atoms, and c) at least one monomer C chosen from N-vinyllactams and derivatives thereof, and at least one organic solvent phase comprising at least one first organic solvent, wherein the at least one organic solvent phase comprises less than or equal to 15% by weight of solvents chosen from lower monoalcohols comprising from 1 to 5 carbon atoms and $C_3$-$C_4$ ketones, relative to the total weight of the composition. Advantageously, the monomer C is present in a numerical proportion ranging from 1% to 15% and better still from 5% to 15% relative to the total number of monomers in the polymer.

We have found that polymers and compositions according to the invention provide, among many other benefits, the important benefits of thermal stability at temperatures up to about 375° F. The polymers and compositions thereof may therefore be advantageously used in various industrial applications, particularly in oilfield operations. Non-limiting examples of oilfield applications include anti-settling agents in cementing fluids and rheology modifiers and/or fluid loss control additives in drilling fluids.

SUMMARY

In a first aspect, the invention provides a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker.

In a second aspect, the invention provides a composition comprising a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker. Non-limiting examples of such compositions include oilfield compositions, drilling fluids, drilling muds, cementing fluids, servicing fluids, gravel packing muds, fracturing fluids, completion fluids, workover fluids, spacer fluids, personal care compositions, coating compositions, household, industrial and institutional compositions, pharmaceutical compositions, food compositions, construction compositions, biocides, adhesives, inks, papers, polishes, membranes, metal working fluids, plastics, textiles, printing compositions, lubricants, preservatives, agrochemicals, and wood-care compositions. Particularly, the composition is an oilfield composition.

In a third aspect, the invention provides an oilfield composition comprising a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker. Particularly, the oilfield composition is a drilling fluid, fracturing fluid, cementing fluid, servicing fluid, gravel packing mud, completion fluid, workover fluid, or spacer fluid.

In a forth aspect, the invention provides a drilling fluid comprising a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker.

In a fifth aspect, the invention provides a cementing fluid comprising a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker.

In a sixth aspect, the invention provides a fracturing fluid comprising a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker.

In a seventh aspect, the invention provides a servicing fluid comprising a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker.

In an eighth aspect, the invention provides a method of cementing a subterranean zone penetrated by a well bore, comprising (A) providing a cementing fluid comprising a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker; (B) placing the cementing fluid into the subterranean zone; and (C) allowing the cementing fluid to set.

In a ninth aspect, the invention provides a method of controlling fluid loss from a well bore into a subterranean zone, comprising (A) providing a drilling fluid comprising a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker; and (B) placing the drilling fluid into the subterranean zone.

DETAILED DESCRIPTION

Before explaining at least one aspect of the disclosed and/or claimed inventive concept(s) in detail, it is to be understood that the disclosed and/or claimed inventive concept(s) is not limited in its application to the details of construction and the arrangement of the components or steps or methodologies set forth in the following description. The disclosed and/or claimed inventive concept(s) is capable of other aspects or of being practiced or carried out in various ways. Also, it is to be understood that the phraseology and terminology employed herein is for the purpose of description and should not be regarded as limiting.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications referenced in any portion of this application are herein expressly incorporated by reference herein their entirety to the same extent as if each individual patent or publication was specifically and individually indicated to be incorporated by reference.

All of the articles and/or methods disclosed herein can be made and executed without undue experimentation in light of the present disclosure. While the articles and methods of the disclosed and/or claimed inventive concept(s) have been described in terms of particular aspects, it will be apparent to those of ordinary skill in the art that variations may be applied to the articles and/or methods and in the steps or in the sequence of steps of the method described herein without departing from the concept, spirit and scope of the disclosed and/or claimed inventive concept(s).

All such similar substitutes and modifications apparent to those skilled in the art are deemed to be within the spirit, scope and concept of the disclosed and/or claimed inventive concept(s).

As utilized in accordance with the disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or."

Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, $B_{Xn}$, $B_{Xn+1}$, or combinations thereof" is intended to include at least one of: A, $B_{Xn}$, $B_{Xn+1}$, $AB_{Xn}$, $AB_{Xn+1}$, $B_{Xn}B_{Xn+1}$, or $AB_{Xn}B_{Xn+1}$ and, if order is important in a particular context, also $B_{Xn}A$, $B_{Xn+1}A$, $B_{Xn+1}B_{Xn}$, $B_{Xn+1}B_{Xn}A$, $B_{Xn}B_{Xn+1}A$, $AB_{Xn+1}B_{Xn}$, $B_{Xn}AB_{Xn+1}$, or $B_{Xn+1}AB_{Xn}$. Continuing with this example, expressly included are combinations that contain repeats of one or more item or term, such as $B_{Xn}B_{Xn}$, AAA, $MB_{Xn}$, $B_{Xn}B_{Xn}B_{Xn+1}$, $AAAB_{Xn}B_{Xn+1}B_{Xn+1}B_{Xn+1}$ $B_{Xn+1}$, $B_{Xn+1}B_{Xn}B_{Xn}AAA$, $B_{Xn+1}A$ $B_{Xn}AB_{Xn}B_{Xn}$, and so forth. The skilled artisan will understand that typically there is no limit on the number of items or terms in any combination, unless otherwise apparent from the context.

The term "each independently selected from the group consisting of" means when a group appears more than once in a structure, that group may be selected independently each time it appears.

The term "hydrocarbyl" includes straight-chain and branched-chain alkyl, alkenyl, alkynyl, cycloalkyl, cycloalkenyl, aryl groups, and combinations thereof with optional heteroatom(s). A hydrocarbyl group may be mono-, di- or polyvalent.

The term "alkyl" refers to a functionalized or unfunctionalized monovalent straight-chain or branched-chain $C_1$-$C_{60}$ group optionally having one or more heteroatoms. Particularly, an alkyl is a $C_1$-$C_{45}$ group and more particularly, a $C_1$-$C_{30}$ group. Non-limiting examples of alkyl groups include methyl, ethyl, n-propyl, isopropyl, n-butyl, isobutyl, tert-butyl, n-pentyl, isopentyl, n-hexyl, n-heptyl, n-octyl, 2-ethylhexyl, tert-octyl, iso-norbornyl, n-dodecyl, tert-dodecyl, n-tetradecyl, n-hexadecyl, n-octadecyl, and n-eicosyl.

The term "aryl" refers to a functionalized or unfunctionalized monovalent aromatic hydrocarbyl group optionally having one or more heteroatoms. The definition of aryl also includes heteroaryl groups. Non-limiting examples of aryl groups include phenyl, naphthyl, pyrrolyl, furanyl, thienyl, pyridyl, indolyl, benzofuranyl, benzothiophenyl, quinolinyl, isoquinolinyl, and the like.

The term "alkylene" refers to a functionalized or unfunctionalized divalent straight-chain, branched-chain or cyclic $C_1$-$C_{40}$ group optionally having one or more heteroatoms. Particularly, an alkylene is a $C_1$-$C_{30}$ group and more particularly, a $C_1$-$C_{20}$ group. Non-limiting examples of alkylene groups include —$CH_2$—. —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —$CH_2$—$CH_2$—$CH_2$—$CH_2$—, cyclopropylene, cyclobutylene, cyclopentylene, cyclohexylene groups, and the like.

The term "arylene" refers to a functionalized or unfunctionalized divalent aromatic hydrocarbyl group optionally having one or more heteroatoms. The definition of arylene also includes heteroarylene groups. Non-limiting examples of arylene groups include phenylene, naphthylene, pyridinylene, and the like.

The term "heteroatom" refers to oxygen, nitrogen, sulfur, silicon, phosphorous, and/or halogen. The heteroatom(s) may be present as a part of one or more heteroatom-containing functional groups. Non-limiting examples of heteroatom-containing functional groups include ether, hydroxy, epoxy, carbonyl, carboxamide, carboxylic ester, carboxylic acid, imine, imide, amine, sulfonic, sulfonamide, phosphonic, and silane groups. The heteroatom(s) may also be present as a part of a ring such as in heteroaryl and heteroarylene groups.

The term "halogen" refers to chloro, bromo, iodo and/or fluoro.

The term "ammonium" includes protonated $NH_3$ and protonated primary, secondary, and tertiary organic amines.

The term "functionalized" refers to the state of a moiety that has one or more functional groups introduced to it by way of one or more functionalization reactions known to a person having ordinary skill in the art. Non-limiting examples of functionalization reactions include epoxidation, sulfonation, hydrolysis, amidation, esterification, hydroxylation, dihydroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like.

The term "residue of" refers to a fragment of a reactant that remains after a reaction with another reactant(s). The residue may be mono-, di- or polyvalent.

The term "monomer" refers to a small molecule that chemically bonds during polymerization to one or more monomers of the same or different kind to form a polymer.

The term "polymer" refers to a large molecule comprising one or more types of monomer residues (repeating units) connected by covalent chemical bonds. By this definition, polymer encompasses compounds wherein the number of monomer units may range from very few, which more commonly may be called as oligomers, to very many. Non-limiting examples of polymers include homopolymers, and non-homopolymers such as copolymers, terpolymers, tetrapolymers and the higher analogues. The polymer may have a random, block, and/or alternating architecture.

The term "homopolymer" refers to a polymer that consists essentially of a single monomer type.

The term "non-homopolymer" refers to a polymer that comprises more than one monomer types.

The term "copolymer" refers to a non-homopolymer that comprises two different monomer types.

The term "terpolymer" refers to a non-homopolymer that comprises three different monomer types.

The term "branched" refers to any non-linear molecular structure. The term includes both branched and hyperbranched structures.

The term "free radical addition polymerization initiator" refers to a compound used in a catalytic amount to initiate a free radical addition polymerization. The choice of initiator depends mainly upon its solubility and its decomposition temperature.

The term "alkyl (alk) acrylate" refers to an alkyl ester of an acrylic acid or an alkyl acrylic acid.

The term "alkyl (alk) acrylamide" refers to an alkyl amide of an acrylic acid or an alkyl acrylic acid.

The term "oilfield composition" refers to a composition that may be used in the exploration, extraction, recovery, and/or completion of any hydrocarbon. Non-limiting examples of oilfield compositions include drilling fluids, cementing fluids, anti-agglomerants, kinetic hydrate inhibitors, shale swelling inhibitors, drilling muds, servicing fluids, gravel packing muds, friction reducers, fracturing fluids, completion fluids, and work over fluids.

The term "fluid loss" refers primarily to water loss, but also may include minor amounts of other fluids which are subject to loss.

The term "fracturing" refers to the process and methods of breaking down a geological formation, i.e. the rock formation around a well bore, by pumping a fluid at very high pressures, in order to increase production rates from a hydrocarbon reservoir.

The term "drilling fluid" refers to compositions such as fluids, slurries, or muds used during oil and/or gas well drilling operations.

The term "cementing fluid" refers to compositions such as fluids or slurries used during cementing operations of a well. For example, a cementing fluid may comprise an aqueous fluid and at least one cementitious material.

The term "fracturing fluid" refers to fluids or slurries used downhole during fracturing operations.

The term "servicing fluid" refers to a fluid used to drill, complete, work over, fracture, or in any way prepare a well bore for the recovery of materials residing in a subterranean formation penetrated by the well bore. It is understood that "subterranean formation" encompasses both areas below exposed earth or areas below earth covered by water such as sea or ocean water. Examples of servicing fluids include, but are not limited to, a drilling fluid or mud, a cement slurry, a gravel packing fluid, a fracturing fluid, a completion fluid, and a work-over fluid, all of which are well known in the art.

The terms "personal care composition" and "cosmetics" refer to compositions intended for use on or in the human body, such as skin, sun, hair, oral, cosmetic, and preservative compositions, including those to alter the color and appearance of the skin and hair.

The term "pharmaceutical composition" refers to any composition comprising at least one pharmaceutically active ingredient, as well as any product which results, directly or indirectly, from combination, complexation, or aggregation of any two or more of the ingredients, from dissociation of one or more of the ingredients, or from other types of reactions or interactions of one or more of the ingredients.

All percentages, ratio, and proportions used herein are based on a weight basis unless other specified.

In a first aspect, the invention provides a polymer comprising repeating units derived from at least one monomer comprising at least one functionalized or unfunctionalized acryloyl moiety and at least one lactam moiety (monomer A); at least one monomer comprising at least one sulfonic acid moiety or a salt thereof (monomer $B_{X1}$); and at least one crosslinker (monomer $B_{X2}$).

In particular embodiments, the monomer (monomer A) comprising at least one functionalized or unfunctionalized acryloyl moiety and at least one lactam moiety has the structure:

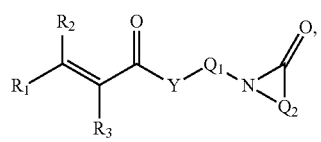

(1)

wherein each $R_1$, $R_2$ and $R_3$ is independently selected from the group consisting of hydrogen, halogens, functionalized and unfunctionalized $C_1$-$C_4$ alkyl, and

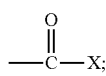

each X is independently selected from the group consisting of $OR_4$, OM, halogen, $N(R_5)(R_6)$,

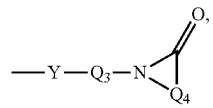

and combinations thereof; each Y is independently oxygen, $NR_7$ or sulfur; each $R_4$, $R_5$, $R_6$ and $R_7$ is independently selected from the group consisting of hydrogen and functionalized and unfunctionalized alkyl; each M is independently selected from the group consisting of metal ions, ammonium ions, organic ammonium cations, and combinations thereof; and each $Q_1$, $Q_2$, $Q_3$, and $Q_4$ is independently selected from the group consisting of functionalized and unfunctionalized alkylene.

Particularly, each $Q_1$, $Q_2$, $Q_3$, and $Q_4$ is independently selected from the group consisting of functionalized and unfunctionalized $C_1$-$C_{12}$ alkylene. Particular, yet non-limiting examples of alkylene groups include —$CH_2$—, —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, and —$CH_2$—$CH_2$—$CH_2$—$CH_2$—$CH_2$—$CH_2$—$CH_2$—.

In one non-limiting embodiment, each $R_1$, $R_2$ and $R_3$ is independently selected from the group consisting of hydrogen, methyl and combinations thereof. Particularly, $R_1$ and $R_2$ are hydrogens and $R_3$ is hydrogen or methyl.

In another non-limiting embodiment, each $R_1$ and $R_3$ is independently hydrogen or methyl; $R_2$ is

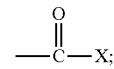

X is selected from the group consisting of $OR_4$, OM, halogens, and $N(R_5)(R_6)$; each $R_4$, $R_5$, and $R_6$ is independently selected from the group consisting of hydrogen and functionalized and unfunctionalized alkyl; and each M is independently selected from the group consisting of metal ions, ammonium ions, organic ammonium cations, and combinations thereof. Particularly, $R_1$ and $R_3$ are hydrogens and $R_2$ is

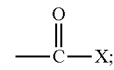

X is selected from the group consisting of $OR_4$, OM and $N(R_5)(R_6)$; each $R_4$, $R_5$, and $R_6$ is independently selected from the group consisting of hydrogen and functionalized and unfunctionalized $C_1$-$C_4$ alkyl; and each M is independently selected from the group consisting of metal ions, ammonium ions, organic ammonium cations, and combinations thereof.

The first polymerizable unit, defined by structure (1), may be synthesized using methods recorded in the art, e.g., by reaction of an N-hydroxylalkyl lactam with an acrylate, (meth)acrylate, anhydride, or similar compounds. Production methods include those described in U.S. Pat. Nos. 2,882,262; 5,523,340; 6,369,163; U.S. Patent Application Publication 2007/123673; GB 924,623; 930,668; and 1,404, 989; WO 03/006569; and EP 385918. Each of the previous disclosures are hereby incorporated herein by reference in its entirety.

The lactam-containing monomers shown in structures (2)-(57) can be obtained from condensation reactions that include an N-hydroxyalkyl lactam and an unsaturated carboxylic acid, an acrylate, a (meth)acrylate, or an anhydride. Suitable N-hydroxyalkyl lactams include N-hydroxymethyl pyrrolidone and caprolactam, N-hydroxyethyl pyrrolidone and caprolactam, and N-hydroxypropyl pyrrolidone and caprolactam. Non-limiting examples of carboxylic acids that can be used include: acrylic acid, methacrylic acid, itaconic acid, crotonic acid, fumaric acid, succinic acid, and maleic acid. Similarly, acrylates and (meth)acrylates include (without limitation) methyl, ethyl, butyl, octyl, ethyl hexyl acrylates and their (meth)acrylate analogues. Representative anhydrides include formic anhydride, succinic anhydride, maleic anhydride and acetic anhydride.

In particular embodiments, the monomer having at least one functionalized or unfunctionalized acryloyl moiety and at least one lactam moiety (monomer A) has a structure selected from the group consisting of:

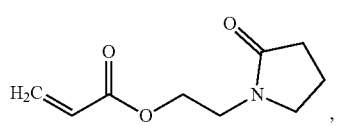
(2)

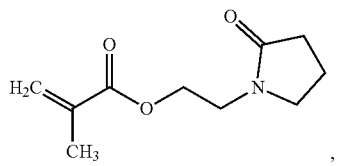
(3)

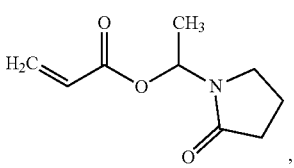
(4)

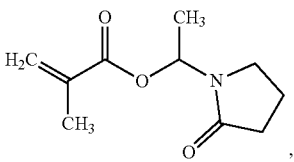
(5)

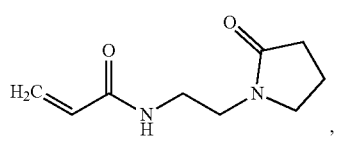
(6)

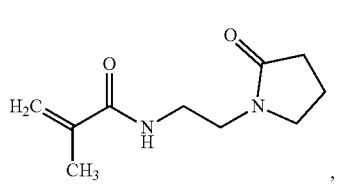
(7)

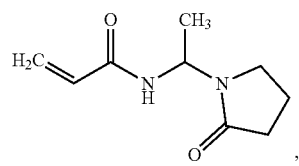
(8)

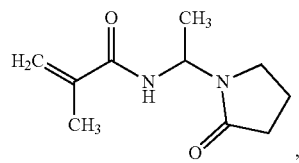
(9)

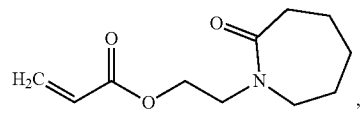
(10)

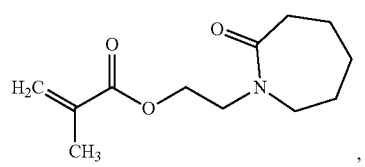
(11)

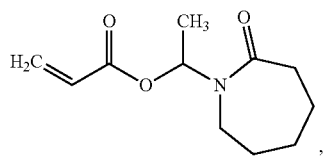
(12)

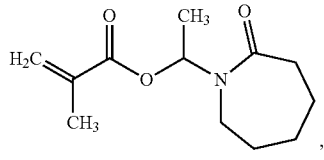
(13)

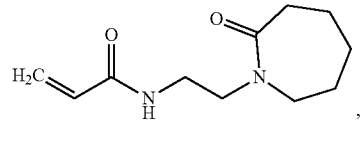
(14)

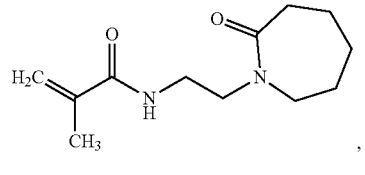
(15)

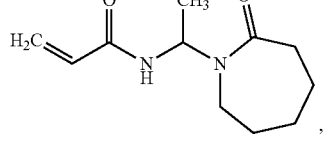
(16)

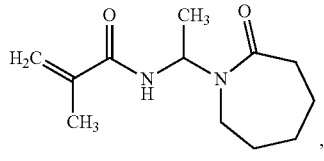
(17)

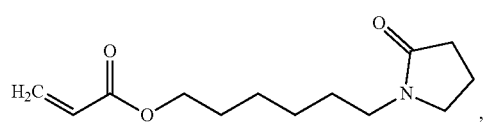 (18)
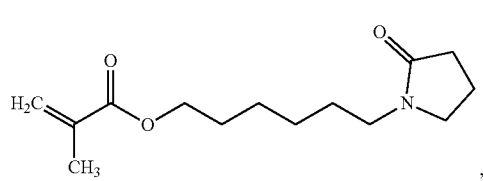 (19)
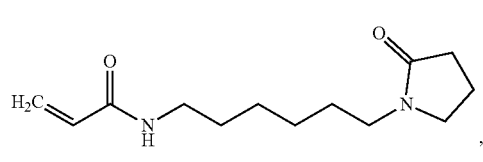 (20)
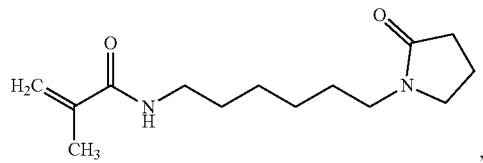 (21)
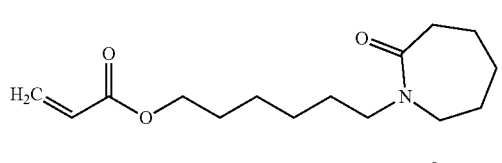 (22)
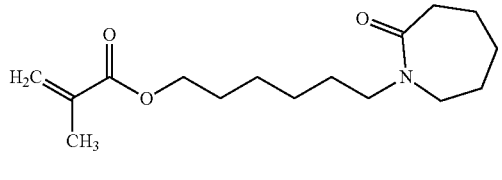 (23)
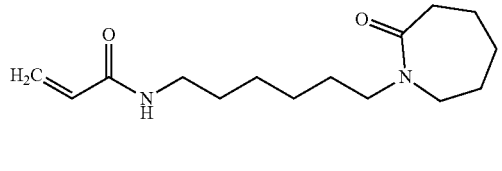 (24)
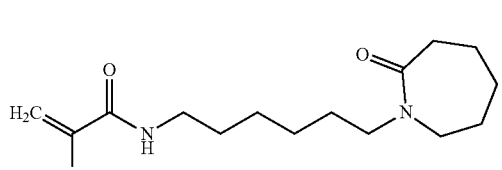 (25)
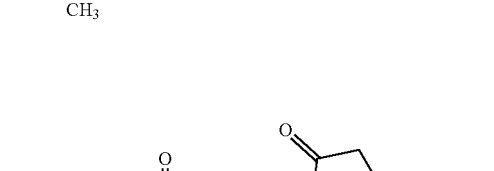 (26)
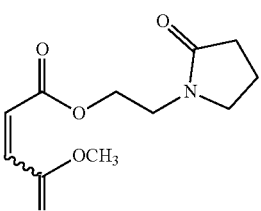 (27)
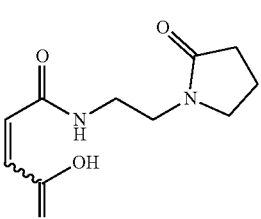 (28)
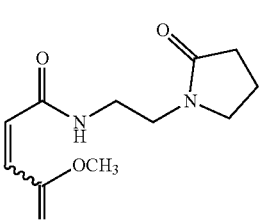 (29)
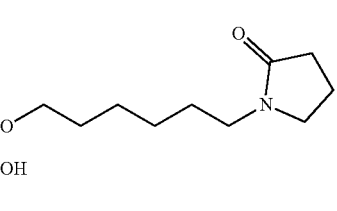 (30)
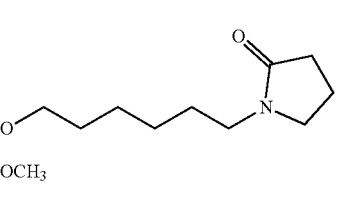 (31)
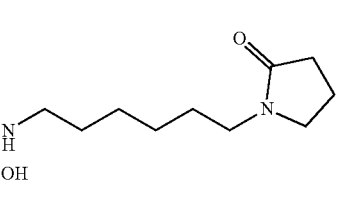 (32)
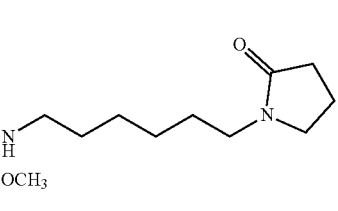 (33)

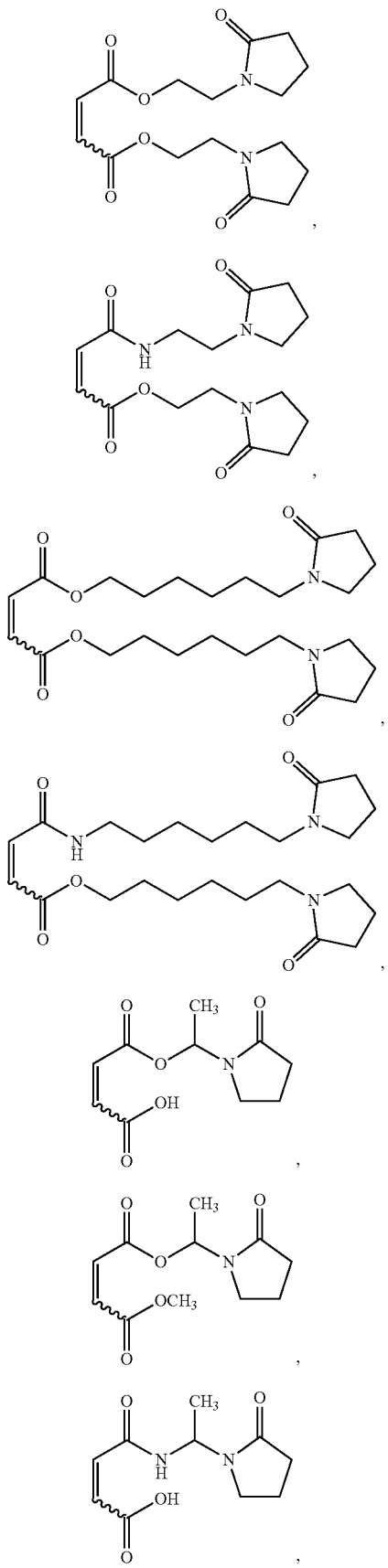
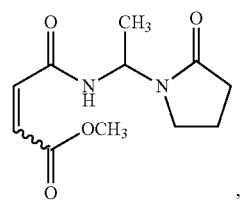
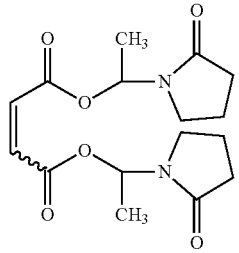
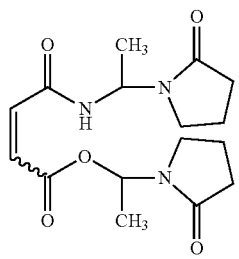
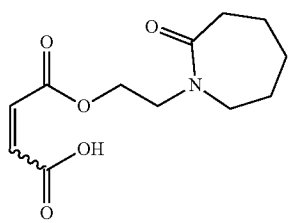
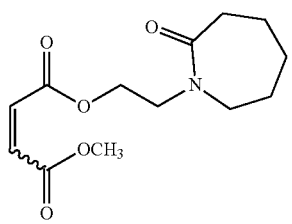
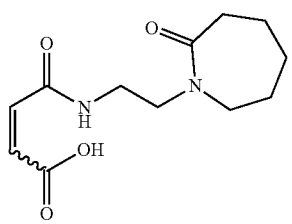
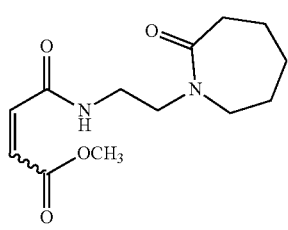

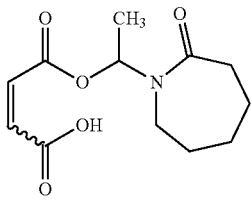 (48)

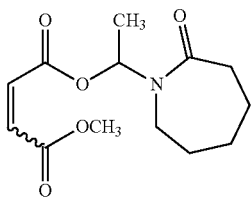 (49)

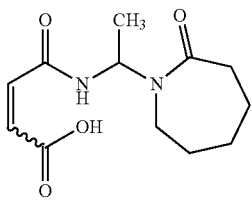 (50)

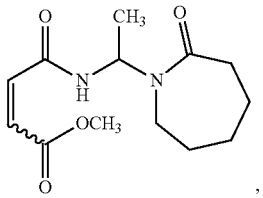 (51)

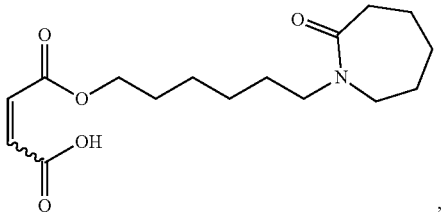 (52)

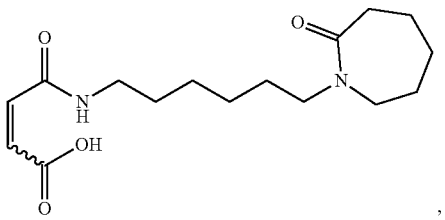 (53)

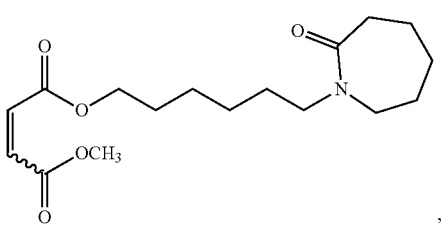 (54)

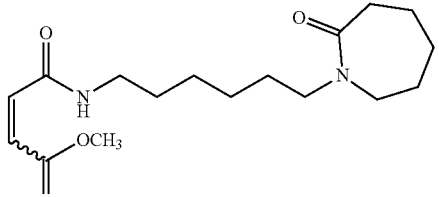 (55)

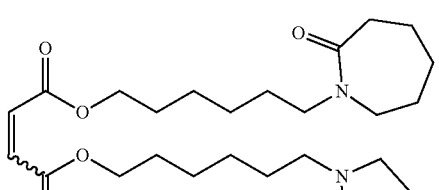 (56)

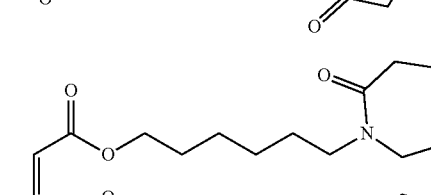 , and

 (57)

Other suitable examples of can be found in WO 2011/063208, the disclosure of which is hereby incorporated herein by reference in its entirety.

In particular embodiments, the monomer comprising at least one sulfonic acid moiety or a salt thereof (monomer $B_{X1}$) has a structure selected from the group consisting of:

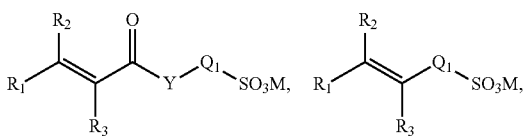

and combinations thereof, wherein each $R_1$, $R_2$ and $R_3$ is independently selected from the group consisting of hydrogen, halogens, functionalized and unfunctionalized $C_1$-$C_4$ alkyl, and combinations thereof; Y is oxygen or $NR_4$; $R_4$ is hydrogen or functionalized and unfunctionalized alkyl; $Q_1$ is a functionalized or unfunctionalized alkylene; $Q_2$ is a direct bond or is selected from the group consisting of functionalized and unfunctionalized alkylenes, arylenes, and combinations thereof; and each M is independently selected from the group consisting of hydrogen, alkali metal ions, alkaline earth metal ions, transition metal ions, ammonium ions, organic ammonium cations, and combinations thereof.

Particular, yet non-limiting examples of monomers comprising at least one sulfonic acid moiety or a salt thereof (monomer $B_{X1}$) are selected from the group consisting of 2-acrylamido-2-methyl propane sulfonic acid, 2-acrylamido-2-ethyl propane sulfonic acid, 2-acrylamido-2-propyl propane sulfonic acid, 2-methacrylamido-2-methyl propane sulfonic acid, 2-methacrylamido-2-ethyl propane sulfonic acid, 3-methacrylamido-2-hydroxy-1-propanesulfonic acid, 2-methacrylamido-2-propyl propane sulfonic acid, N-methyl-2-acrylamido-2-methyl propane sulfonic acid, N-methyl-2-acrylamido-2-ethyl propane sulfonic acid, N-methyl-2-acrylamido-2-propyl propane sulfonic acid, N-methyl-2-methacrylamido-2-methyl propane sulfonic acid, N-methyl-2-methacrylamido-2-ethyl propane sulfonic acid, N-methyl-2-methacrylamido-2-propyl propane sulfonic acid, 2-acrylamido-1-butane sulfonic acid, 2-acrylamido-1-pentane sulfonic acid, 2-acrylamido-1-hexane sulfonic acid, 2-methacrylamido-1-butane sulfonic acid, 2-methacrylamido-1-pentane sulfonic acid, 2-methacrylamido-1-hexane sulfonic acid, 2-acrylamido-1-heptane sulfonic acid, 2-methacrylamido-1-heptane sulfonic acid, N-methyl-2-acrylamido-1-butane sulfonic acid, N-methyl-2-methacrylamido-1-butane sulfonic acid, N-methyl-2-acrylamido-1-pentane sulfonic acid, N-methyl-2-methacrylamido-1-pentane sulfonic acid, N-methyl-2-acrylamido-1-hexane sulfonic acid, N-methyl-2-methacrylamido-1-hexane sulfonic acid, N-methyl-2-acrylamido-1-heptane sulfonic acid, N-methyl-2-methacrylamido-1-heptane sulfonic acid, vinyl sulfonic acid, allyl sulfonic acid, allyloxybenzenesulfonic acid, 2-methyl-2-propene-1-sulfonic acid, methallylsulfonic acid, styrenesulfonic acid, salts thereof, and combinations thereof. Particularly, the monomer comprising at least one sulfonic acid moiety or a salt thereof is selected from the group consisting of 2-acrylamido-2-methyl propane sulfonic acid, 2-methacrylamido-2-methyl propane sulfonic acid, vinyl sulfonic acid, allyl sulfonic acid, methallylsulfonic acid, styrenesulfonic acid, and combinations thereof.

Particular, yet non limiting examples of crosslinkers (monomer $B_{X2}$) include: divinyl ethers of compounds selected from the group consisting of ethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-unidecanediol, 1,12-dodecanediol, and combinations thereof; divinyl ethers of diethylene glycol, triethylene glycol, tetraethylene glycol, pentaethylene glycol, hexaethylene glycol, heptaethylene glycol, octaethylene glycol, nonaethylene glycol, decaethylene glycol, and polyalkylene glycols; methylenebis(meth)acrylamide; ethylene glycol di(meth)acrylate; butanediol di(meth)acrylate; tetraethylene glycol di(meth)acrylate; polyethylene glycol di(meth)acrylate; polyethylene glycol di(meth)acrylamide; dipropylene glycol diallyl ether; polyglycol diallyl ether; hydroquinone diallyl ether; trimethylolpropane tri(meth) acrylate; trimethylolpropane diallyl ether; pentaerythritol triallyl ether; allyl(meth)acrylate; triallyl cyanurate; diallyl maleate; polyallyl esters; tetraallyloxyethane; triallylamine; tetraallylethylenediamine; divinyl benzene; glycidyl (meth)acrylate; 1,7-octadiene; 1,9-decadiene; 1,13-tetradecadiene; divinylbenzene; diallyl phthalate; triallyl-1,3,5-triazine-2,4,6(1H,3H,5H)-trione; N,N'-divinylimidazolidone; 1-vinyl-3(E)-ethylidene pyrrolidone; 2,4,6-triallyloxy-1,3,5-triazine; and combinations thereof. More particularly, the crosslinker is selected from the group consisting of: pentaerythritol triallyl ether, trimethylolpropane diallyl ether, trimethylolpropane tri(meth)acrylate, methylenebis(meth)acrylamide, ethylene glycol di(meth)acrylate, ethylene glycol di(meth)acrylamide, butanediol di(meth)acrylate, polyethylene glycol di(meth)acrylate, polyethylene glycol di(meth)acrylamide, and combinations thereof. Even more particularly, the crosslinker is selected from the group consisting of: pentaerythritol triallyl ether, trimethylolpropane diallyl ether, trimethylolpropane tri(meth)acrylate, methylenebis(meth) acrylamide, and combinations thereof.

Particularly, the crosslinker(s) may be present in an amount from about 0.001% by weight to about 20% by weight of the polymer. More particularly, the crosslinker(s) may be present in an amount from about 0.001% by weight to about 10% by weight of the polymer. Even more particularly, the crosslinker(s) may be present in an amount from about 0.001% by weight to about 5% by weight of the polymer.

In a particular, yet non-limiting embodiment, the polymer according to the invention comprises repeating units derived from: from about 0.1 to about 99.9 percent by weight of the polymer of at least one monomer comprising at least one functionalized or unfunctionalized acryloyl moiety and at least one lactam moiety (monomer A); (b) from about 0.1 to about 99.9 percent by weight of the polymer of at least one monomer comprising at least one sulfonic acid moiety or a salt thereof (monomer $Bx_1$); and (c) from about 0.01 to about 20 percent by weight of the polymer of at least one crosslinker (monomer $B_{X2}$), with the proviso that the sum of the percent by weight values of the monomers and the crosslinker(s) is equal to 100.

More particularly, the polymer comprises repeating units derived from: from about 0.1 to about 20 percent by weight of the polymer of at least one monomer (monomer A) having a structure selected from the group consisting of

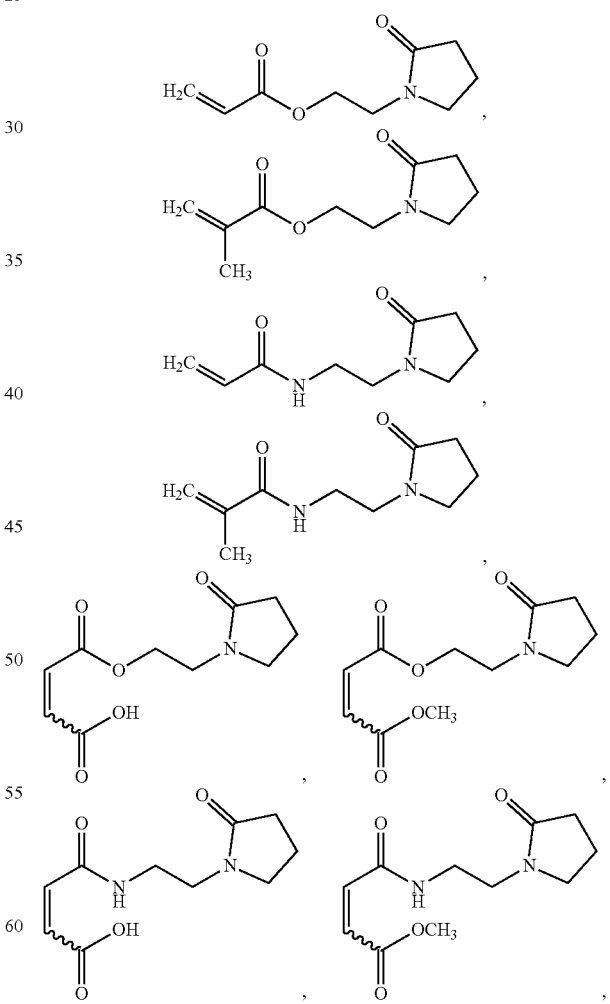

and combinations thereof; (b) from about 80 to about 99.9 percent by weight of the polymer of at least one monomer (monomer $B_{X1}$) selected from the group consisting of 2-acrylamido-2-methyl propane sulfonic acid, 2-methacrylamido-2-methyl propane sulfonic acid, vinyl sulfonic acid, salts thereof, and combinations thereof; and (c) from about 0.01 to about 20 percent by weight of the polymer of at least one crosslinker (monomer $B_{X2}$) selected from the group consisting of pentaerythritol triallyl ether, methylenebis(meth)acrylamide, and combinations thereof, with the proviso that the sum of the percent by weight values of the monomers and the crosslinker(s) is equal to 100.

In particular embodiments, the polymer according to the invention (inventive polymer) further comprises repeating units derived from at least one monomer selected from the group consisting of functionalized and unfunctionalized N-vinyl lactams, N-vinyl-2-pyrrolidone, N-vinylcaprolactam, alkyl vinyl ethers, methyl vinyl ether, isobutyl vinyl ether, vinyl alkanoates, vinyl acetate, vinyl alkanamides, vinyl alcohols, vinyl carbonates, vinyl carbamates, vinyl thiocarbamates, vinyl ureas, vinyl halides, vinyl imidazoles, vinyl pyridines, vinyl silanes, vinyl siloxanes, vinyl sulfones, maleic anhydride, maleates, fumarates, maleimides, maleamic acids, alpha-olefins, isobutylene, vinyl triazoles, alpha, beta-olefinically unsaturated carboxylic nitriles, acrylonitrile, styrenes, and combinations thereof.

The polymers according to the invention may be used alone or in combination with other ingredient(s) in various compositions and product forms.

In a second aspect, the invention provides a composition comprising a polymer comprising repeating units derived from at least one monomer comprising at least one functionalized or unfunctionalized acryloyl moiety and at least one lactam moiety (monomer A); at least one monomer comprising at least one sulfonic acid moiety or a salt thereof (monomer $B_{X1}$); and at least one crosslinker. Particular, yet non-limiting examples of such compositions include oilfield compositions, drilling fluids, drilling muds, cementing fluids, servicing fluids, gravel packing muds, fracturing fluids, completion fluids, workover fluids, spacer fluids, personal care compositions, coating compositions, household, industrial and institutional compositions, pharmaceutical compositions, food compositions, construction compositions, biocides, adhesives, inks, papers, polishes, membranes, metal working fluids, plastics, textiles, printing compositions, lubricants, preservatives, agrochemicals, and wood-care compositions.

In a third aspect, the invention provides an oilfield composition comprising a polymer comprising repeating units derived from at least one monomer comprising at least one functionalized or unfunctionalized acryloyl moiety and at least one lactam moiety (monomer A); at least one monomer comprising at least one sulfonic acid moiety or a salt thereof (monomer $B_{X1}$); and at least one crosslinker (monomer $B_{X2}$). Particularly, the oilfield composition is a drilling fluid, fracturing fluid, cementing fluid, servicing fluid, gravel packing mud, completion fluid, workover fluid, or spacer fluid.

In particular embodiments, the polymer according to the invention is present in an amount from about 0.01 percent to about 20 percent by weight of the oilfield composition. More particularly, the polymer is present in an amount from about 0.05 percent to about 10 percent by weight of the oilfield composition. Even more particularly, the polymer is present in an amount from about 0.1 percent to about 5 percent by weight of the oilfield composition.

In particular embodiments, the oilfield compositions may further comprise one or more additives. Particular, yet non-limiting examples of such additives include secondary fluid loss control agents, secondary cement anti-settling agents, agents for delayed crosslinking, weighting agents, silica flour, strength enhancers, rheology modifiers, friction reducers, dispersing agents, surfactants, clathrate hydrate inhibitors, shale swelling inhibitors, gelation inhibitors, gas migration control additives, set retarding agents, accelerants, activators, defoaming agents, lost circulation materials, corrosion inhibitors, salts, strength retrogression additives, vitrified shale, thixotropic additives, and combinations thereof.

In a forth aspect, the invention provides a drilling fluid comprising a polymer comprising repeating units derived from at least one monomer comprising at least one functionalized or unfunctionalized acryloyl moiety and at least one lactam moiety (monomer A); at least one monomer comprising at least one sulfonic acid moiety or a salt thereof (monomer $Bx_1$); and at least one crosslinker (monomer $B_{X2}$).

In particular embodiments, the polymer according to the invention is present in an amount from about 0.01 percent to about 20 percent by weight of the drilling fluid. More particularly, the polymer is present in an amount from about 0.05 percent to about 10 percent by weight of the drilling fluid. Even more particularly, the polymer is present in an amount from about 0.1 percent to about 5 percent by weight of the drilling fluid.

In a fifth aspect, the invention provides a cementing fluid comprising a polymer comprising repeating units derived from at least one monomer comprising at least one functionalized or unfunctionalized acryloyl moiety and at least one lactam moiety (monomer A); at least one monomer comprising at least one sulfonic acid moiety or a salt thereof (monomer $B_{X1}$); and at least one crosslinker (monomer $B_{X2}$).

In particular embodiments, the polymer according to the invention is present in an amount from about 0.01 percent to about 20 percent by weight of the cementing fluid. More particularly, the polymer is present in an amount from about 0.05 percent to about 10 percent by weight of the cementing fluid. Even more particularly, the polymer is present in an amount from about 0.1 percent to about 5 percent by weight of the cementing fluid.

In particular embodiments, the cementing fluids may further comprise at least one additive selected from the group consisting of: weighting agents, silica flour, strength enhancers, fluid loss control agents, surface rheology control additives, friction reducers, dispersing agents, gelation inhibitors, gas migration control additives, set retarding agents, accelerants, defoaming agents, lost circulation materials, corrosion inhibitors, salts, fly ash, fiber, strength retrogression additives, vitrified shale, lightweight additives, thixotropic additives, secondary cement anti-settling additives, and combinations thereof.

The amount of each additive in the cementing fluid, when present, may vary depending on the type of composition, the function and/or physicochemical property of the additive, and the amount of other co-ingredients.

Any of a variety of cementitious materials suitable for use in subterranean cementing operations may be used in accordance with particular aspects of the invention. Suitable non-limiting examples include hydraulic cements that comprise calcium, aluminum, silicon, oxygen, and/or sulfur, which set and harden by reaction with water. Such hydraulic cements, include, but are not limited to, Portland cements, pozzolana cements, gypsum cements, high alumina content cements, slag cements, and silica cements, and combinations thereof. Particularly, the cementitious material is a hydraulic cement. More particularly, the cementitious material is Portland cement.

In a sixth aspect, the invention provides a fracturing fluid comprising a polymer comprising repeating units derived from at least one monomer comprising at least one functionalized or unfunctionalized acryloyl moiety and at least one lactam moiety (monomer A); at least one monomer comprising at least one sulfonic acid moiety or a salt thereof (monomer $B_{X1}$); and at least one crosslinker (monomer $B_{X2}$).

In particular embodiments, the polymer according to the invention is present in an amount from about 0.01 percent to about 20 percent by weight of the fracturing fluid. More particularly, the polymer is present in an amount from about 0.05 percent to about 10 percent by weight of the fracturing fluid. Even more particularly, the polymer is present in an amount from about 0.1 percent to about 5 percent by weight of the fracturing fluid.

In a seventh aspect, the invention provides a servicing fluid comprising a polymer comprising repeating units derived from at least one monomer comprising at least one functionalized or unfunctionalized acryloyl moiety and at least one lactam moiety (monomer A); at least one monomer comprising at least one sulfonic acid moiety or a salt thereof (monomer $B_{X1}$); and at least one crosslinker (monomer $B_{X2}$).

In particular embodiments, the polymer according to the invention is present in an amount from about 0.01 percent to about 20 percent by weight of the servicing fluid. More particularly, the polymer is present in an amount from about 0.05 percent to about 10 percent by weight of the servicing fluid. Even more particularly, the polymer is present in an amount from about 0.1 percent to about 5 percent by weight of the servicing fluid.

In an eighth aspect, the invention provides a method of cementing a subterranean zone penetrated by a well bore, comprising (A) providing a cementing fluid comprising a polymer comprising repeating units derived from at least one monomer comprising at least one functionalized or unfunctionalized acryloyl moiety and at least one lactam moiety (monomer A); at least one monomer comprising at least one sulfonic acid moiety or a salt thereof (monomer $B_{X1}$); and at least one crosslinker (monomer $B_{X2}$); (B) placing the cementing fluid into the subterranean zone; and (C) allowing the cementing fluid to set.

In a ninth aspect, the invention provides a method of controlling fluid loss from a well bore into a subterranean zone, comprising (A) providing a drilling fluid comprising a polymer comprising repeating units derived from at least one monomer comprising at least one functionalized or unfunctionalized acryloyl moiety and at least one lactam moiety; at least one monomer comprising at least one sulfonic acid moiety or a salt thereof; and at least one crosslinker; and (B) placing the drilling fluid into the subterranean zone.

Methods of Synthesis

The polymers according to the invention may be readily synthesized by procedures known by those skilled in the art, non-limiting examples of which include free radical polymerization, dispersion polymerization, emulsion polymerization, ionic chain polymerization, living polymerization, and precipitation polymerization.

Free radical polymerization may be used, especially when using water-dispersible and/or water-soluble reaction solvent(s). This type of polymerization method is described in "Decomposition Rate of Organic Free Radical Polymerization" by K. W. Dixon (section II in Polymer Handbook, volume 1, 4th edition, Wiley-Interscience, 1999), the disclosure of which is hereby incorporated herein by reference in its entirety.

Compounds capable of initiating the free-radical polymerization include those materials known to function in the prescribed manner, and include the peroxo and azo classes of materials. Peroxo and azo compounds include, but are not limited to: acetyl peroxide; azo bis-(2-amidinopropane) dihydrochloride; azo bis-isobutyronitrile; 2,2'-azo bis-(2-methylbutyronitrile); benzoyl peroxide; di-tert-amyl peroxide; di-tert-butyl diperphthalate; butyl peroctoate; tert-butyl dicumyl peroxide; tert-butyl hydroperoxide; tert-butyl perbenzoate; tert-butyl permaleate; tert-butyl perisobutylrate; tert-butyl peracetate; tert-butyl perpivalate; para-chlorobenzoyl peroxide; cumene hydroperoxide; diacetyl peroxide; dibenzoyl peroxide; dicumyl peroxide; didecanoyl peroxide; dilauroyl peroxide; diisopropyl peroxodicarbamate; dioctanoyl peroxide; lauroyl peroxide; octanoyl peroxide; succinyl peroxide; and bis-(ortho-toluoyl) peroxide. Also suitable to initiate the free-radical polymerization are initiator mixtures or redox initiator systems, including: ascorbic acid/iron (II) sulfate/sodium peroxodisulfate, tert-butyl hydroperoxide/sodium disulfite, and tert-butyl hydroperoxide/sodium hydroxymethanesulfinate.

The polymerization reactions may be carried out in the presence of solvent(s). The polymers may be synthesized in a solvent and maintained therein, or the synthesis solvent separated from the polymer by methods known in the art and replaced by a solvent beneficial for formulary development and/or end-use. The polymerization temperature may vary from about 5° C. to about 200° C. The polymerization reaction may be carried out at ambient pressure, sub-atmospheric pressure, or super-atmospheric pressure. The polymerization reaction may be carried out in a batch, continuous or semi-continuous manner.

Characterization of Polymers

The polymers and compositions according to the invention may be analyzed by known techniques. Especially preferred are the techniques of $^{13}C$ nuclear magnetic resonance (NMR) spectroscopy, gas chromatography (GC), and gel permeation chromatography (GPC) in order to decipher polymer identity, residual monomer concentrations, polymer molecular weight, and polymer molecular weight distribution.

Nuclear magnetic resonance (NMR) spectroscopy is an especially preferred method to probe the polymerization product in terms of chemical properties such as monomeric composition, sequencing and tacticity. Analytical equipment suitable for these analyses includes the Inova 400-MR NMR System by Varian Inc. (Palo Alto, Calif.). References broadly describing NMR include: Yoder, C. H. and Schaeffer Jr., C. D., *Introduction to Multinuclear NMR*, The Benjamin/Cummings Publishing Company, Inc., 1987; and Silverstein, R. M., et al., *Spectrometric Identification of Organic Compounds*, John Wiley & Sons, 1981, the disclosure of which is hereby incorporated herein by reference in its entirety.

Residual monomer levels can be measured by GC, which can be used to indicate the extent of reactant conversion by the polymerization process. GC analytical equipment to perform these tests are commercially available, and include the following units: Series 5880, 5890, and 6890 GC-FID and GC-TCD by Agilent Technologies, Inc. (Santa Clara, Calif.). GC principles are described in *Modern Practice of Gas Chromatography*, third edition (John Wiley & Sons, 1995) by Robert L. Grob and Eugene F. Barry, the disclosure of which is hereby incorporated herein by reference in its entirety.

GPC is an analytical method that separates molecules based on their hydrodynamic volume (or size) in solution of the mobile phase, such as hydroalcoholic solutions with surfactants. GPC is a preferred method for measuring polymer molecular weight distributions. This technique can be performed on known analytical equipment sold for this purpose, and include the TDAmax™ Elevated Temperature GPC System and the RImax™ Conventional Calibration System by Viscotek™ Corp. (Houston, Tex.). In addition, GPC employs analytical standards as a reference, of which a plurality of narrow-distribution polyethylene glycol and polyethylene oxide standards representing a wide range in molecular weight is the preferred. These analytical standards are available for purchase from Rohm & Haas Company (Philadelphia, Pa.) and Varian Inc. (Palo Alto, Calif.). GPC is described in the following texts, the disclosure of which is hereby incorporated herein by reference in its entirety: Schroder, E., et al., *Polymer Characterization*, Hanser Publishers, 1989; Billingham, N.C., *Molar Mass Measurements in Polymer Science*, Halsted Press, 1979; and Billmeyer, F., *Textbook of Polymer Science*, Wiley Interscience, 1984.

The polymers according to the invention may be prepared according to the procedures set out below. The examples are presented for purposes of demonstrating, but not limiting, the preparation of the polymers. Therein, the following abbreviations are used:

PyEMA: Pyrrolidonylethyl methacrylate
AMPS: 2-acrylamido-2-methyl-1-propanesulfonic acid
NaAMPS: Sodium salt of 2-acrylamido-2-methyl-1-propanesulfonic acid
MBA: Methylenebisacrylamide
PAE: Pentaerythritol allyl ether
HTHP: High Temperature/High Pressure
HT: High Temperature
PV: Plastic Viscosity
YP: Yield Point
API: American Petroleum Institute
RT: Room Temperature

EXAMPLES

Example 1

An amount of 74.9 g of AMPS and 510 g of tert-butanol was added to a 1 liter four-necked reactor. The reaction mixture was neutralized with 25.2 g of ammonium hydroxide (28-30% in $H_2O$). The reaction vessel was then equipped with thermocouple, cold water condenser, and anchor agitator before heating reaction to 68° C. Once all pellets of AMPS were dissolved, pH value of the mixture was tested and kept in the range of 6.5 to 7.5. The reactor was then charged with 0.82 g of MBA that has been fully solubilized in 5 g and 5 g tert-butanol. An amount of 7.5 g of PAE and 7.7 g PyEMA were then charged into reactor. Subsurface $N_2$ sparge was then introduced to reactor. An amount of 0.2828 g of Trigonox® 25C75/2 g tert-butanol was charged into reactor (time t=0). Within 30 minutes, white precipitated particles were visible. An additional shot of 0.2828 g Trigonox® 25C75/2 g tert-butanol was added 2 hours later (t=2). At t=3 hours, the reaction temperature was then increased to 80° C. One hour later (t=4), a final shot of 0.15 g Trigonox® 25C75/2 g tert-butanol was added. The reaction was held for 2 additional hours (t=6), then cooled and discharged. The resultant polymer powder was filtered using Buchner funnel and washed three times with approximately 50 mL of hot tert-butanol. The polymer was transferred to a baking dish to dry further in an 80° C. vacuum oven with a vacuum of approximately 20 torr overnight.

Example 2

An amount of 78.5 g of AMPS and 510 g of tert-butanol was added to a 1 liter four-necked reactor. The reaction mixture was neutralized with 26.6 g of ammonium hydroxide (28-30% in $H_2O$). The reaction vessel was then equipped with thermocouple, cold water condenser, and anchor agitator before heating reaction to 68° C. Once all pellets of AMPS were dissolved, pH value of the mixture was tested and kept in the range of 6.5 to 7.5. The reactor was then charged with 0.82 g of MBA that has been fully solubilized in 5 g and 5 g tert-butanol. An amount of 7.5 g of PAE and 4.13 g PyEMA were then charged into reactor. Subsurface $N_2$ sparge was then introduced to reactor. An amount of 0.2828 g of Trigonox® 25C75/2 g tert-butanol was charged into reactor (time t=0). Within 30 minutes, white precipitated particles were visible. An additional shot of 0.2828 g Trigonox® 25C75/2 g tert-butanol was added 2 hours later (t=2). At t=3 hours, the reaction temperature was then increased to 80° C. One hour later (t=4), a final shot of 0.15 g Trigonox® 25C75/2 g tert-butanol was added. The reaction was held for 2 additional hours (t=6), then cooled and discharged. The resultant polymer powder was filtered using Buchner funnel and washed three times with approximately 50 mL of hot tert-butanol. The polymer was transferred to a baking dish to dry further in an 80° C. vacuum oven with a vacuum of approximately 20 torr overnight.

Example 3

An amount of 80.9 g of AMPS and 510 g of tert-butanol was added to a 1 liter four-necked reactor. The reaction mixture was neutralized with 27.3 g of ammonium hydroxide (28-30% in $H_2O$). The reaction vessel was then equipped with thermocouple, cold water condenser, and anchor agitator before heating reaction to 68° C. Once all pellets of AMPS were dissolved, pH value of the mixture was tested and kept in the range of 6.5 to 7.5. The reactor was then charged with 0.82 g of MBA that has been fully solubilized in 5 g and 5 g tert-butanol. An amount of 7.5 g of PAE and 1.7 g PyEMA were then charged into reactor. Subsurface $N_2$ sparge was then introduced to reactor. An amount of 0.2828 g of Trigonox® 25C75/2 g tert-butanol was charged into reactor (time t=0). Within 30 minutes, white precipitated particles were visible. An additional shot of 0.2828 g Trigonox® 25C75/2 g tert-butanol was added 2 hours later (t=2). At t=3 hours, the reaction temperature was then increased to 80° C. One hour later (t=4), a final shot of 0.15 g Trigonox® 25C75/2 g tert-butanol was added. The reaction was held for 2 additional hours (t=6), then cooled and discharged. The resultant polymer powder was filtered using Buchner funnel and washed three times with approximately 50 mL of hot tert-butanol. The polymer was transferred to a baking dish to dry further in an 80° C. vacuum oven with a vacuum of approximately 20 torr overnight.

Example 4

An amount of 74.9 g of AMPS and 510 g of tert-butanol was added to a 1 liter four-necked reactor. The reaction mixture was neutralized with 25.2 g of ammonium hydroxide (28-30% in $H_2O$). The reaction vessel was then equipped with thermocouple, cold water condenser, and anchor agitator before heating reaction to 68° C. Once all pellets of AMPS were dissolved, pH value of the mixture was tested and kept in the range of 6.5 to 7.5. The reactor was then charged with 0.41 g of MBA that has been fully solubilized in 5 g and 5 g tert-butanol. An amount of 3.3 g of PAE and 7.7 g PyEMA were then charged into reactor. Subsurface $N_2$ sparge was then introduced to reactor. An amount of 0.2828 g of Trigonox® 25C75/2 g tert-butanol was charged into reactor (time t=0). Within 30 minutes, white precipitated particles were visible. An additional shot of 0.2828 g Trigonox® 25C75/2 g tert-butanol was added 2 hours later (t=2). At t=3 hours, the reaction temperature was then increased to 80° C. One hour later (t=4), a final shot of 0.15 g Trigonox® 25C75/2 g tert-butanol was added. The reaction was held for 2 additional hours (t=6), then cooled and discharged. The resultant polymer powder was filtered using Buchner funnel and washed three times with approximately 50 mL of hot tert-butanol. The polymer was transferred to a baking dish to dry further in an 80° C. vacuum oven with a vacuum of approximately 20 torr overnight.

Example 5

An amount of 74.9 g of AMPS and 510 g of tert-butanol was added to a 1 liter four-necked reactor. The reaction mixture was neutralized with 25.2 g of ammonium hydroxide (28-30% in $H_2O$). The reaction vessel was then equipped with thermocouple, cold water condenser, and anchor agitator before heating reaction to 68° C. Once all pellets of AMPS were dissolved, pH value of the mixture was tested and kept in the range of 6.5 to 7.5. The reactor was then charged with 0.41 g of MBA that has been fully solubilized in 5 g and 5 g tert-butanol. An amount of 3.3 g of PAE and 7.7 g PyEMA were then charged into reactor. Subsurface $N_2$ sparge was then introduced to reactor. An amount of 0.2828 g of Trigonox® 25C75/2 g tert-butanol was charged into reactor (time t=0). Within 30 minutes, white precipitated particles were visible. An additional shot of 0.2828 g Trigonox® 25C75/2 g tert-butanol was added 2 hours later (t=2). At t=3 hours, the reaction temperature was then increased to 80° C. One hour later (t=4), a final shot of 0.15 g Trigonox® 25C75/2 g tert-butanol was added. The reaction was held for 2 additional hours (t=6), then cooled and discharged. The resultant polymer powder was filtered using Buchner funnel and washed three times with approximately 50 mL of hot tert-butanol. The polymer was transferred to a baking dish to dry further in an 80° C. vacuum oven with a vacuum of approximately 20 torr overnight.

Table 1 shows a summary of reaction conditions for cross-linked polymers of AMPS and PyEMA prepared by precipitation polymerization in tert-butanol

TABLE 1

Reaction Conditions Summary

| Example | Reaction Temperature/ Chasing Temperature | Reaction Time | Reactant Weight Ratio (%) | | | |
|---|---|---|---|---|---|---|
| | | | AMPS | PyEMA | PAE | MBA |
| 1 | 68° C./80° C. | 6 hours | 90 | 10 | 9 | 1 |
| 2 | 68° C./80° C. | 6 hours | 95 | 5 | 9 | 1 |
| 3 | 68° C./80° C. | 6 hours | 98 | 2 | 9 | 1 |
| 4 | 68° C./80° C. | 6 hours | 90 | 10 | 4 | 0.5 |
| 5 | 68° C./80° C. | 6 hours | 90 | 10 | 7 | 0.5 |

Drilling Fluids

Example 6

Five drilling fluid (mud) Formulations numbered 1-5 as shown in Table 2 were prepared on a 600 g scale incorporating polymers from aforementioned synthetic examples. Sufficient mixing was conducted to facilitate dissolving all the ingredients. The drilling fluids were allowed to agitate for 5 to 15 minutes between the addition of each component and with 20 to 40 minutes total for complete and homogenous mixing. Rheological properties were then measured on a Fann 35 before hot rolling (BHR) and after hot rolling (AHR), or before static aging (BSA) and after static aging (ASA). The testing results are shown in Table 2.

TABLE 2

Study of Exemplary Polymers in 12 ppg Drilling Muds Containing 8.6 bl/gal KCl

| Ingredients | Mixing time | Formulation 1 | Formulation 2 | Formulation 3 | Formulation 4 | Formulation 5 |
|---|---|---|---|---|---|---|
| 8.6 ppg KCl, ml | — | 289 | 289 | 289 | 289 | 289 |
| Polymer of Example 1, ppb | 10 min | 6 | — | — | — | — |
| Polymer of Example 2, ppb | 10 min | — | 5 | — | — | — |
| Polymer of Example 3, ppb | 10 min | — | — | 6 | — | — |
| Polymer of Example 4, ppb | 10 min | — | — | — | 6 | — |
| Polymer of Example 5, ppb | 10 min | — | — | — | — | 6 |

TABLE 2-continued

Study of Exemplary Polymers in 12 ppg Drilling Muds Containing 8.6 bl/gal KCl

| Ingredients | Mixing time | Formulation 1 | | Formulation 2 | | Formulation 3 | | Formulation 4 | | Formulation 5 | |
|---|---|---|---|---|---|---|---|---|---|---|---|
| NaOH, 50% | 30 sec | 1 drop | | 1 drop | | 1 drop | | 1 drop | | 1 drop | |
| API Barite, ppb | 10 min | 180 | | 180 | | 180 | | 180 | | 180 | |
| Aging condition | | 350° F. hot rolling/ 16 hours | | | | 375° F. static aging/16 hours | | | | | |
| Fann Data @ RT | | BHR | AHR | BSA | ASA | BSA | ASA | BSA | ASA | BSA | ASA |
| 600 rpm | | 55 | 89 | 52 | 19 | 66 | 73 | 36 | 53 | 44 | 54 |
| 300 rpm | | 38 | 66 | 36 | 12 | 48 | 48 | 26 | 34 | 34 | 36 |
| 200 rpm | | 31 | 55 | 29 | 9 | 37 | 37 | 21 | 26 | 26 | 27 |
| 100 rpm | | 24 | 44 | 22 | 6 | 26 | 25 | 16 | 18 | 20 | 17 |
| 6 rpm | | 13 | 20 | 12 | 3 | 10 | 8 | 7 | 4 | 10 | 4 |
| 3 rpm | | 12. | 18 | 11 | 2 | 9 | 7 | 6 | 3 | 9 | 3 |
| PV, cps | | 17 | 23 | 16 | 7 | 18 | 25 | 10 | 19 | 10 | 18 |
| YP, lb/100 ft$^2$ | | 21 | 43 | 20 | 5 | 30 | 23 | 16 | 15 | 24 | 18 |
| HTHP filtration, 350° F./500 psi, ml/30 min | | — | — | N/A | | — | 10 | | 13.6 | — | 19.2 |

Table 2 demonstrates that polymers according to the invention are thermally stable up to 375° F. They are effective as HTHP fluid loss control additives and have utility as HT rheology modifiers up to 375° F.

Cementing Fluids

Example 7

15.8 ppg of H class cement slurries were formulated using components and mixing/formulation techniques commonly employed in the industry as recommended by American Petroleum Institute. Their rheologies were recorded on an Ofite viscometer before and after conditioning at 190° F. as shown in Table 3.

Table 3 demonstrates that polymers according to the invention are hydrated at 190° F. and have utility as anti-settling agent in cement slurries.

What is claimed is:
1. An oilfield composition comprising a polymer,
  wherein the composition is a cementing fluid, a fracturing fluid, a servicing fluid, a gravel packing mud, a completion fluid, a workover fluid, or a spacer fluid;
  wherein said polymer is present in an amount from about 0.01% by weight to about 20% by weight of said composition;
  said polymer having repeating units derived from
  (a) at least one monomer comprising at least one functionalized or unfunctionalized acryloyl moiety and at

TABLE 3

Study of Exemplary Polymers in 15.8 ppg H Cement Containing 35% Silica Flour

| | Test Sample | | | | | |
|---|---|---|---|---|---|---|
| | Polymer of Example 2, 0.5 bwoc %* | | Polymer of Example 3, 0.5 bwoc % | | Polymer of Example 4, 0.5 bwoc % | |
| | Temp. | | | | | |
| | Ambient | 190° F. | Ambient | 190° F. | Ambient | 190° F. |
| 300 rpm | 130.3 | 307.8 | 100.9 | 195.7 | 125.7 | 228.5 |
| 200 rpm | 96.1 93.6 | 260.1 242.8 | 66.6 70.7 | 154.6 151.8 | 82.4 91.3 | 180.4 173.9 |
| 100 rpm | 55.9 51.8 | 190.9 173.8 | 33.9 34.8 | 101.6 97.9 | 42.9 47.2 | 117.1 110.1 |
| 60 rpm | 38.8 33.7 | 157.9 140.9 | 20.2 20.5 | 74.5 70.8 | 25.3 27.9 | 85.4 78.1 |
| 30 rpm | 25.1 19.7 | 125.7 110.3 | 9.3 9.3 | 47.9 45.8 | 11.5 12.5 | 55.7 48.5 |
| 6 rpm | 11.6 9.8 | 74.2 64.8 | 1.6 1.4 | 22.8 20.5 | 1.4 1.6 | 18.1 16.9 |
| 3 rpm | 8.1 7.8 | 69.6 49.9 | 0.6 0.7 | 17.9 16.9 | 0.7 0.7 | 11.7 10.7 |
| 600 rpm | 213 | 320.2+ | 187.1 | 294.6 | 221.6 | 320.1+ |
| PV, cps | 114.7 | 188.2 | 99.8 | 143.9 | 121.0 | 172.3 |
| YP, lb/100 ft2 | 15.6 | 119.6 | 1.1 | 51.8 | 4.7 | 56.1 |

*bwoc: based on weight of cement least one lactam moiety having a structure selected from the group consisting of:
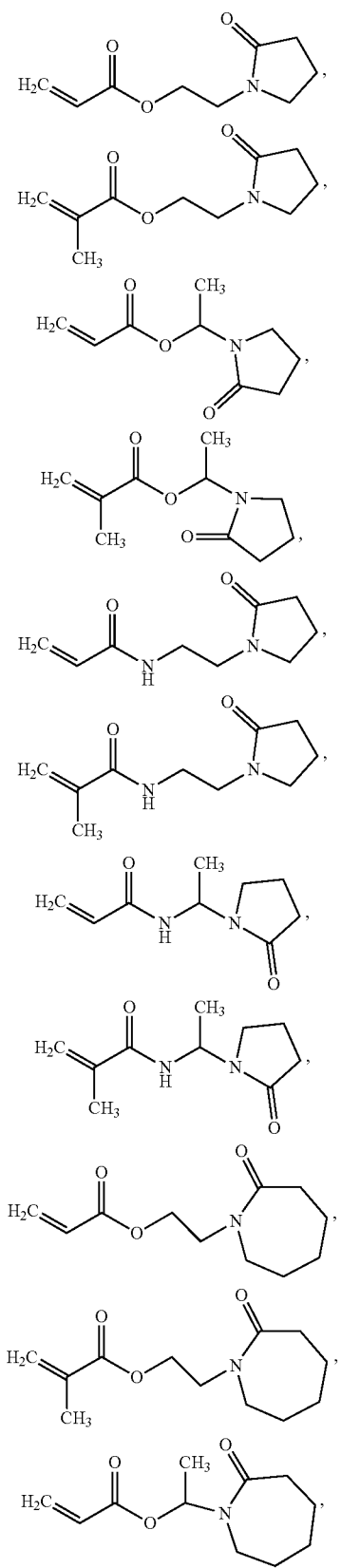
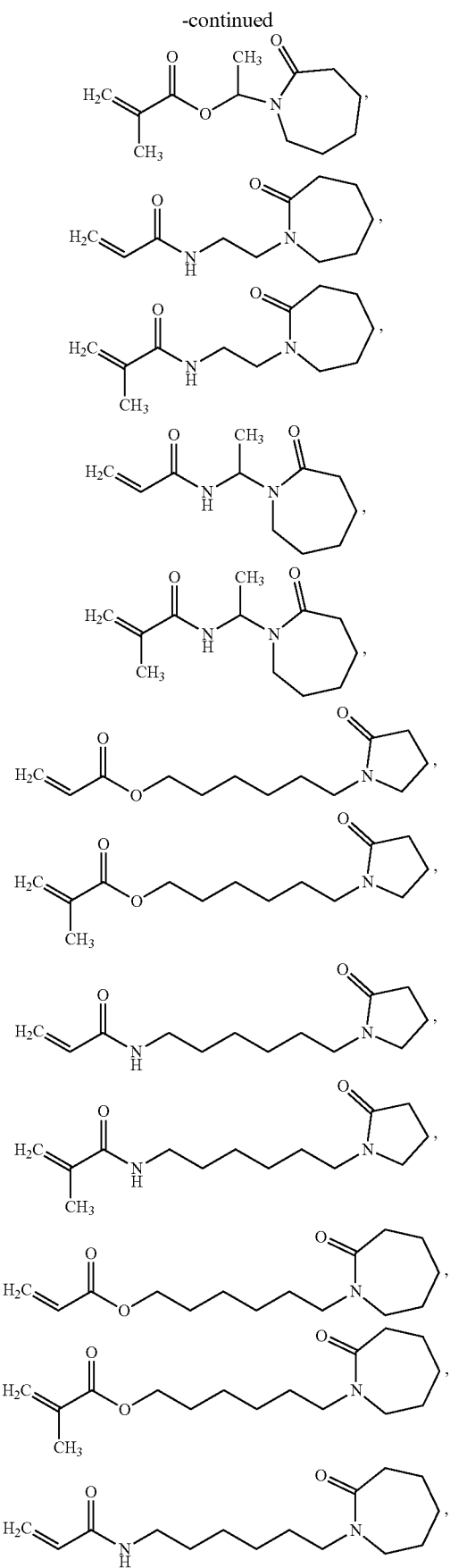

33
-continued
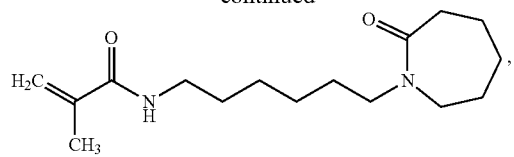
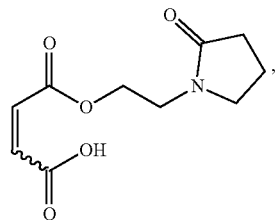
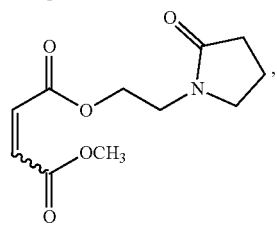
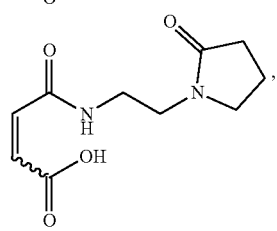
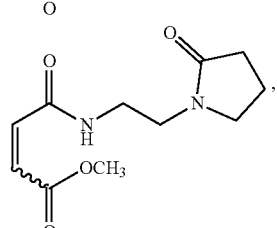
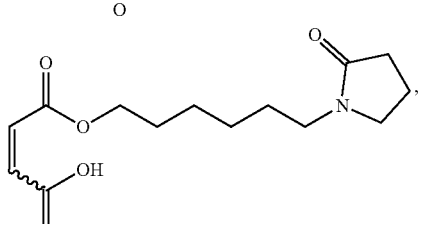
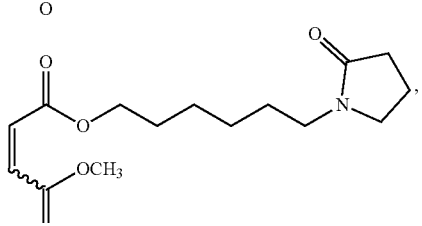
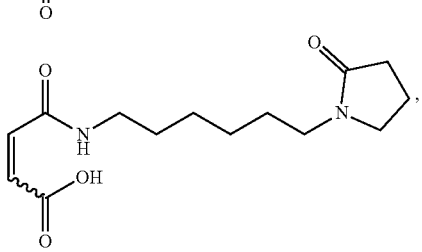
34
-continued
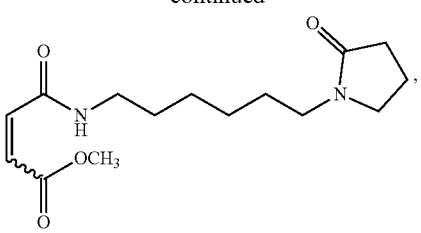
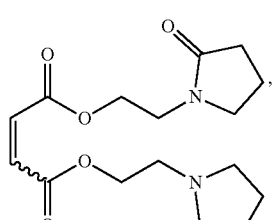
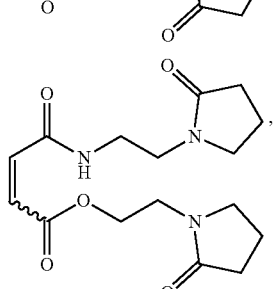
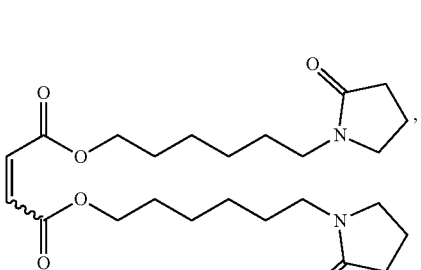
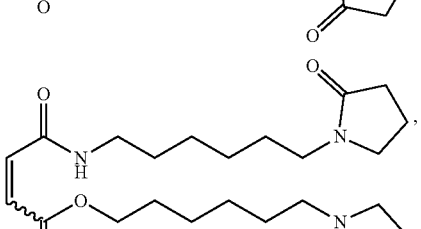
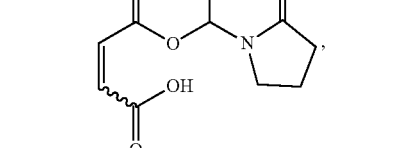
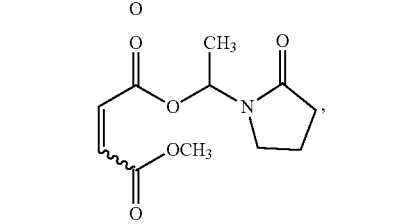

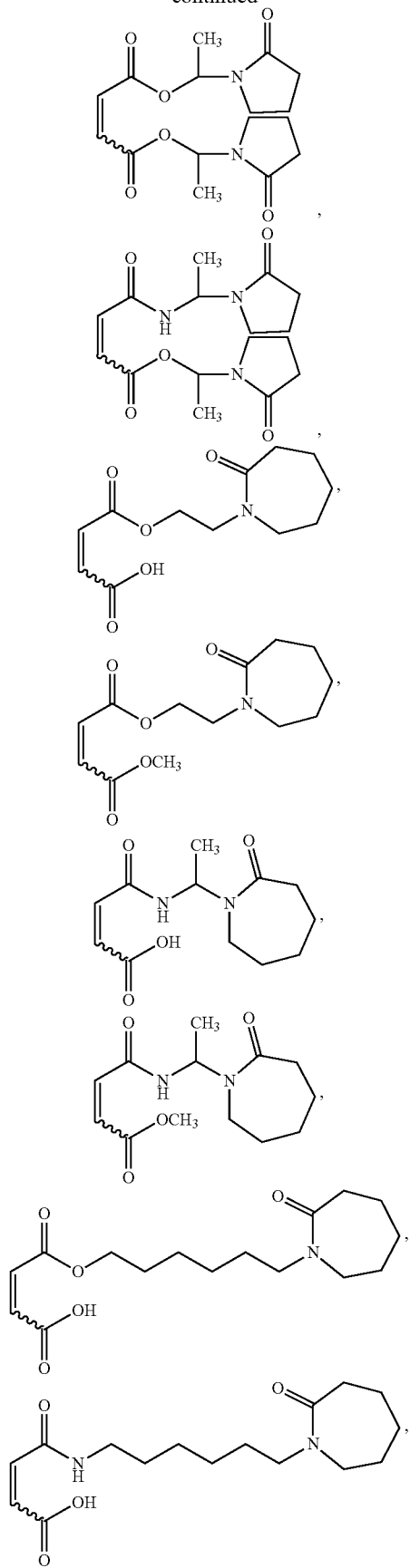

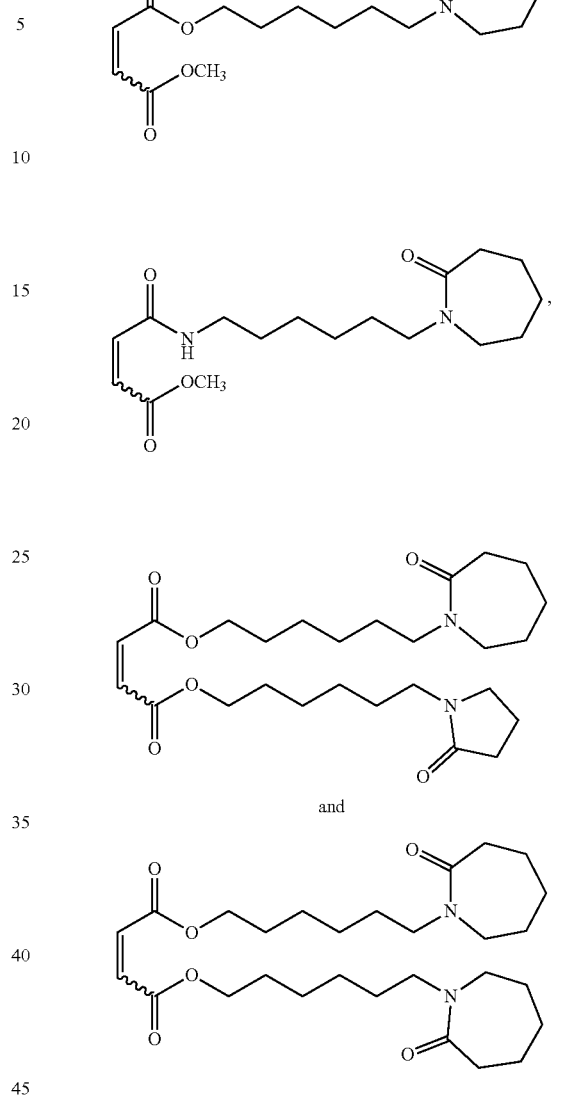

(b) at least one monomer comprising at least one sulfonic acid moiety or a salt thereof; and (c) at least one crosslinker, said oilfield composition further comprising at least one additive selected from the group consisting of secondary fluid loss control agents, secondary cement anti-settling agents, agents for delayed crosslinking, weighting agents, silica flour, strength enhancers, rheology modifiers, friction reducers, dispersing agents, surfactants, clathrate hydrate inhibitors, shale swelling inhibitors, gelation inhibitors, gas migration control additives, set retarding agents, accelerants, activators, defoaming agents, lost circulation materials, corrosion inhibitors, salts, strength retrogression additives, vitrified shale, thixotropic additives, and combinations thereof.

* * * * *